United States Patent
Rao et al.

(10) Patent No.: US 8,957,255 B2
(45) Date of Patent: Feb. 17, 2015

(54) METHOD OF OXIDIZING AN ORGANIC COMPOUND

(71) Applicant: Jawaharlal Nehru Centre for Advanced Scientific Research, Bangalore, Karnataka (IN)

(72) Inventors: Chintamani Nagesa Ramachandra Rao, Karnataka (IN); Ujjal Kam Gautam, Karnataka (IN); Srinivasa Rao Lingampalli, Karnataka (IN)

(73) Assignee: Jawaharlal Nehru Centre for Advanced Scientific Research, Bangalore, Karnataka (IN)

( * ) Notice: Subject to any disclaimer, the term of this patent is extended or adjusted under 35 U.S.C. 154(b) by 0 days.

(21) Appl. No.: 14/046,853

(22) Filed: Oct. 4, 2013

(65) Prior Publication Data

US 2014/0171689 A1   Jun. 19, 2014

Related U.S. Application Data

(60) Provisional application No. 61/733,854, filed on Dec. 5, 2012.

(30) Foreign Application Priority Data

Oct. 5, 2012 (IN) .......................... 4195/CHE/2012

(51) Int. Cl.
C07C 45/28 (2006.01)
C07C 29/48 (2006.01)
C07B 33/00 (2006.01)
C07C 51/285 (2006.01)
C07C 2/84 (2006.01)

(52) U.S. Cl.
CPC ................. *C07B 33/00* (2013.01); *C07C 29/48* (2013.01); *C07C 45/28* (2013.01); *C07C 51/285* (2013.01); *C07C 2/84* (2013.01)
USPC ........................... 568/426; 568/430; 568/815

(58) Field of Classification Search
CPC ...... C07C 45/28; C07C 29/48; C07C 2523/06
USPC .................................................. 568/426, 815
See application file for complete search history.

(56) References Cited

PUBLICATIONS

Enache et al. Solvent-Free Oxidation of Primary Alcohols to Aldehydes Using Au—Pd/TiO2 Catalysts. Science, vol. 311, Jan. 20, 2006, pp. 362-365.*

* cited by examiner

*Primary Examiner* — Sikarl Witherspoon
(74) *Attorney, Agent, or Firm* — Blakely Sokoloff Taylor & Zafman

(57) ABSTRACT

The disclosure relates to a method of oxidation of an aliphatic C—H bond in an organic compound using $CdO_2$ or $ZnO_2$ nanoparticles as oxidizing agents. The instant disclosure relates to a method of oxidizing toluene using metal peroxide nanoparticles such as $CdO_2$, $ZnO_2$ as oxidizing agents to obtain oxidized products predominantly comprising benzaldehyde.

15 Claims, 8 Drawing Sheets

METHOD OF OXIDIZING AN ORGANIC COMPOUND

The following specification particularly describes the invention and the manner in which it is to be performed.

TECHNICAL FIELD

The instant disclosure relates to the field of organic chemistry. Particularly, it pertains to method of selective oxidation of an aliphatic C—H bond in an organic compound using metal peroxide nanoparticle selected from $CdO_2$ or $ZnO_2$ as oxidizing agent.

BACKGROUND OF THE DISCLOSURE

Activation of C—H bond is getting increasing attention in the last few years. Alkyl aromatic compounds such as toluene constitute an important family of compounds and a reaction of great significance in this context is the oxidation of toluene to benzaldehyde and benzyl alcohol. Traditionally, oxidation of toluene has been carried out by the Etard reaction. Commercially, however, benzaldehyde is produced by the bromination or chlorination of toluene followed by saponification. Many other strategies have been reported for the oxidation of toluene and these employ molecular oxygen or other oxidizing agents. Since the oxidizing agents are usually soluble in polar solvents, a second solvent often becomes necessary. Use of toxic solvents is not desirable for several reasons and a number of other approaches have, therefore, been employed. These include use of photocatalysis and ionic liquids. Many of these methods reported in the literature do not show the desired selectivity and yield several products.

Heterogeneous catalysis, which is advantageous due to the ease of separation of the catalysts, has also been employed for the purpose. Thus, single-site heterogeneous catalysts for the solvent-free oxidation of toluene using aluminophosphates have been designed in the prior art. A solvent-free method for the oxidation of toluene in the presence of catalytic Au-Pd alloy nanoparticles has also been reported. However, an over-oxidised product of toluene, benzyl benzoate is obtained as the major product by this method (D. I. Enache et al., Science 2006, Vol. 311, page 362). Further, both $H_2O_2$ and organic peroxides have been used as sources of oxygen for the oxidation of toluene. However, these chemicals are comparatively difficult to store. Other metal peroxides used in the art for oxidising toluene do not give efficient results under 200° C.

In prior art, an additional catalyst is required along with a peroxide for oxidation. Prior literature also discloses that oxygen needs be supplied externally for the oxidation reaction. However, one of the advantages of the instant disclosure is that $CdO_2$ and $ZnO_2$ reactions are not only catalytic in nature, but also act as the source of oxygen. Prior art also depicts that oxidation pertains to pollutants, and thereby small amount of reactants is involved. The present disclosure overcomes these drawbacks such as using organic compound in the entire reaction mixture.

The instant disclosure relates to study of oxidation of toluene using $CdO_2$ and $ZnO_2$ nanoparticles. The oxidation is facile occurring at a temperature range of about 160-180° C. and primarily yielding benzaldehyde. The metal peroxide route is solvent-free and in addition, has several other advantages over some of the methods reported in the literature.

STATEMENT OF THE DISCLOSURE

The present disclosure relates to a method of oxidizing an aliphatic C—H bond in an organic compound, said method comprising acts of mixing the organic compound with metal peroxide nanoparticle selected from group comprising cadmium peroxide or zinc peroxide to obtain reaction mixture, and heating the reaction mixture to obtain oxidized product; and use of metal peroxide nanoparticle selected from group comprising $CdO_2$ or $ZnO_2$, for oxidizing an aliphatic C—H bond in an organic compound to obtain oxidized product.

BRIEF DESCRIPTION OF THE ACCOMPANYING FIGURES

In order that the disclosure may be readily understood and put into practical effect, reference will now be made to exemplary embodiments as illustrated with reference to the accompanying figures. The figure together with a detailed description below, are incorporated in and form part of the specification, and serve to further illustrate the embodiments and explain various principles and advantages, in accordance with the present disclosure where:

Figure 5:
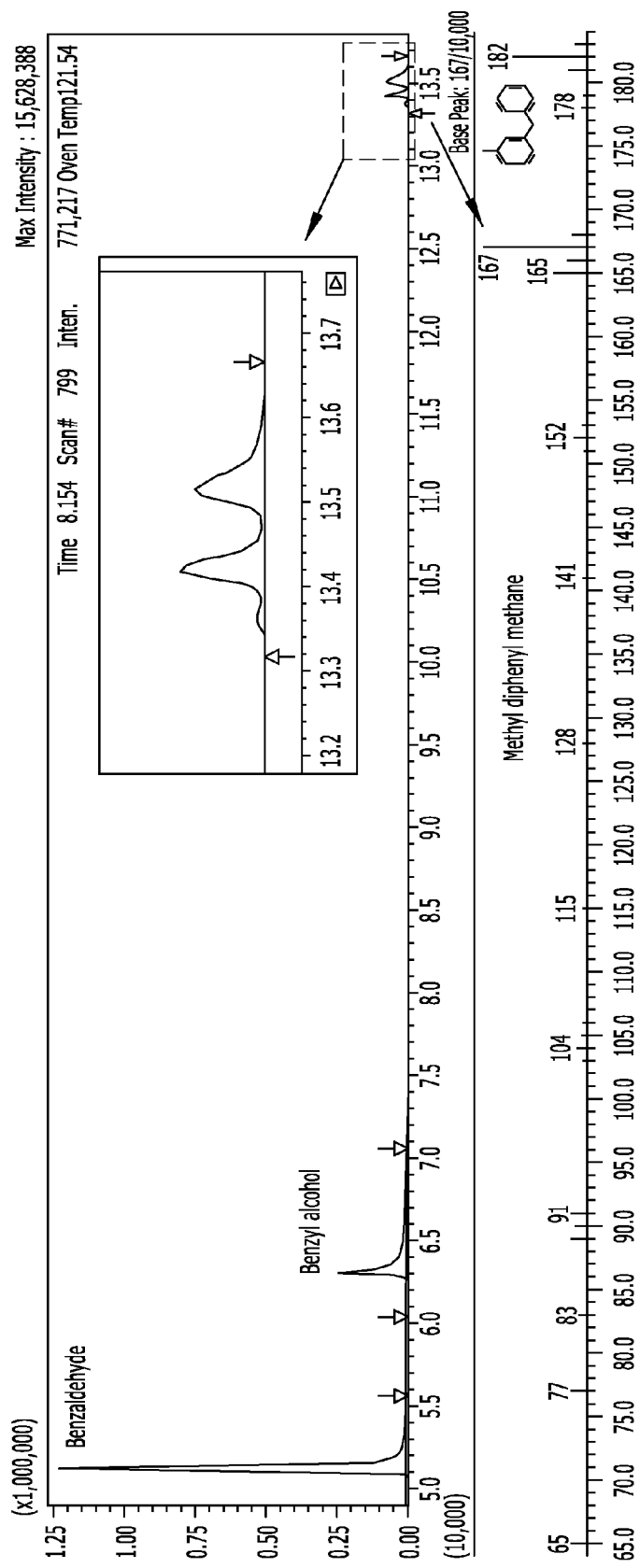

FIG. 5 depicts GC-MS data of the reaction products obtained on oxidation of toluene by $CdO_2$ at about 180° C. for about 4 h. The reaction product contains about 69 % of benzaldehyde, about 26% of benzyl alcohol and about 5% of methyldiphenylmethane or diphenyl ethane.

Figure 6:
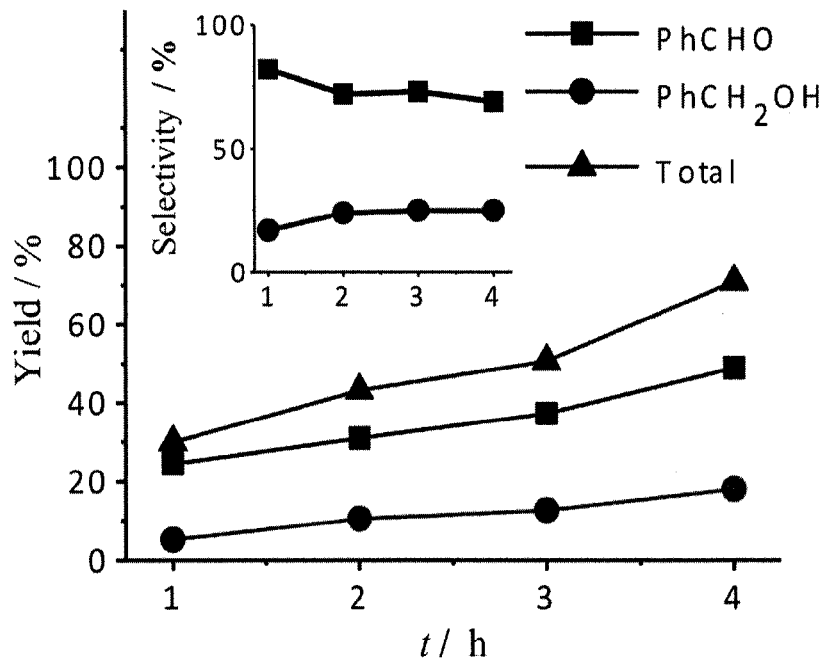
Figure 6:
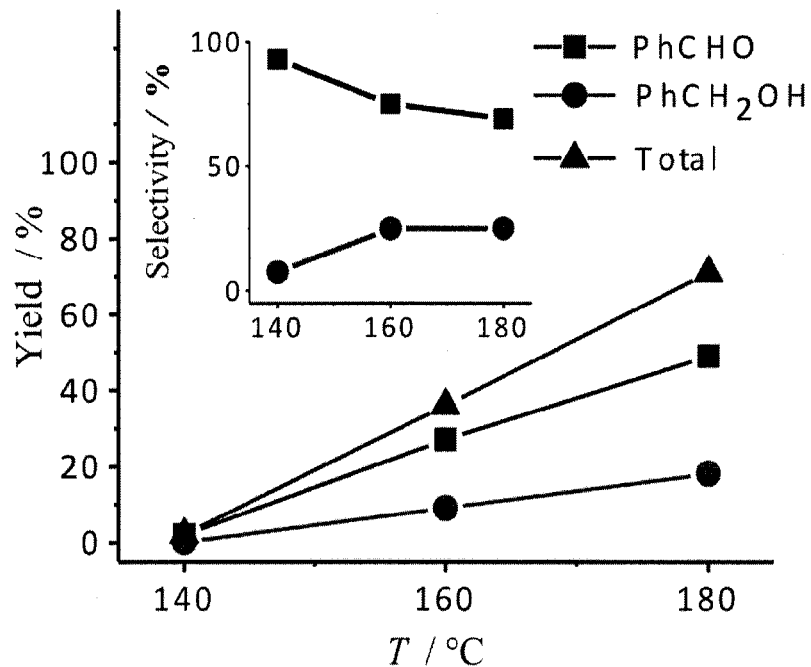

FIG. 6(A) depicts total yield and the relative proportion of the major products of oxidation of toluene by $CdO_2$, (i.e. benzyl alcohol and benzaldehyde) at 180° C. for different reaction times. The inset shows the selectivity of different reaction products.

FIG. 6(B) depicts total yield of the reaction product obtained at various reaction temperatures for a reaction time of 4 h.

Figure 7:
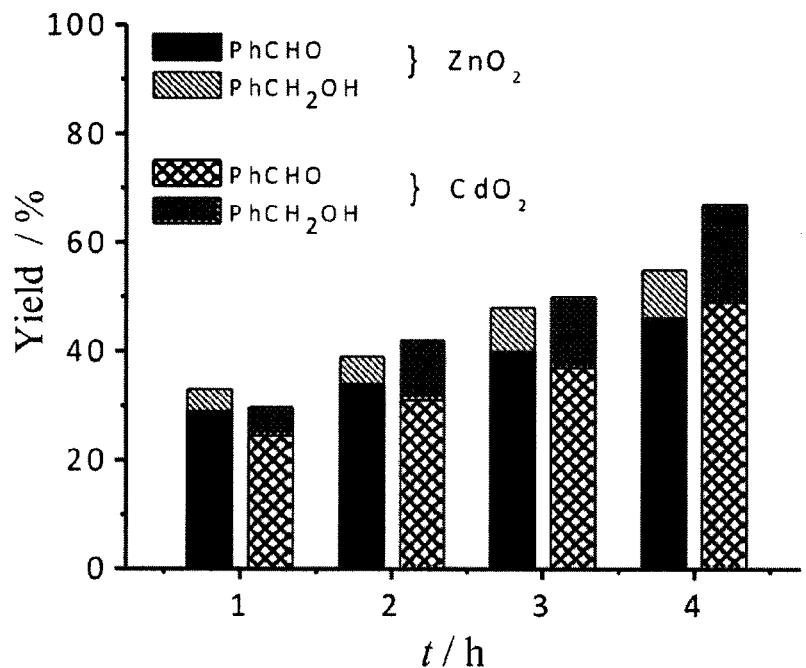
Figure 7:
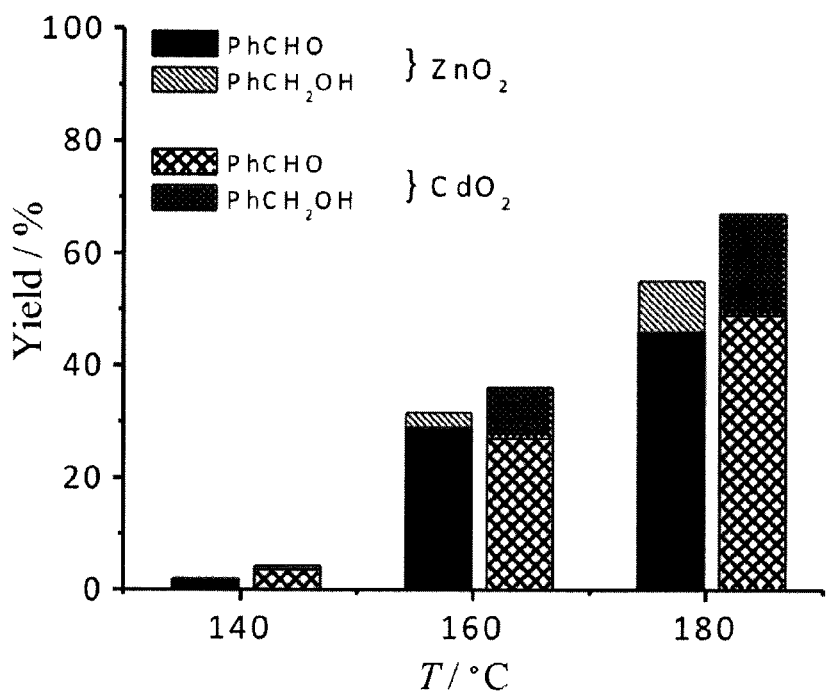

FIG. 7(A) depicts total and relative yields of benzyl alcohol and benzaldehyde produced by the oxidation of toluene by $CdO_2$ and $ZnO_2$ nanoparticles at 180° C. for different reaction times.

FIG. 7(B) depicts total yield of the reaction products obtained at various reaction temperatures for a reaction time of 4 h.

Figure 8:
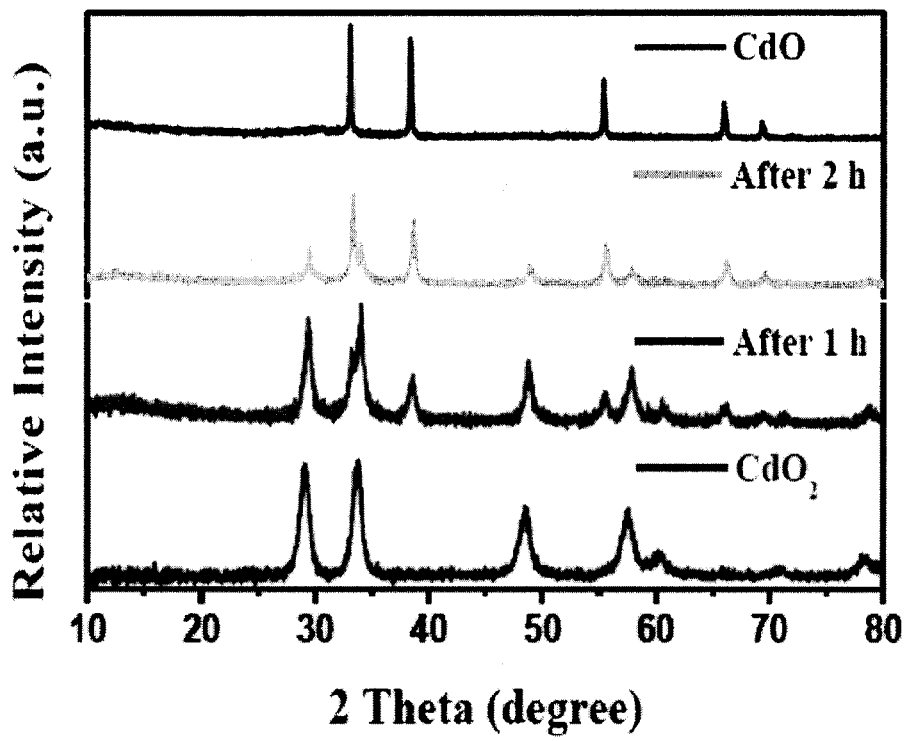

FIG. 8 depicts XRD patterns of the solid product obtained after toluene oxidation carried out at 180° C., in presence of $CdO_2$ after 1 h and 2 h. Unlike fast aerial decomposition of the peroxides, their decomposition in the reaction medium is much slower.

Figure 9:
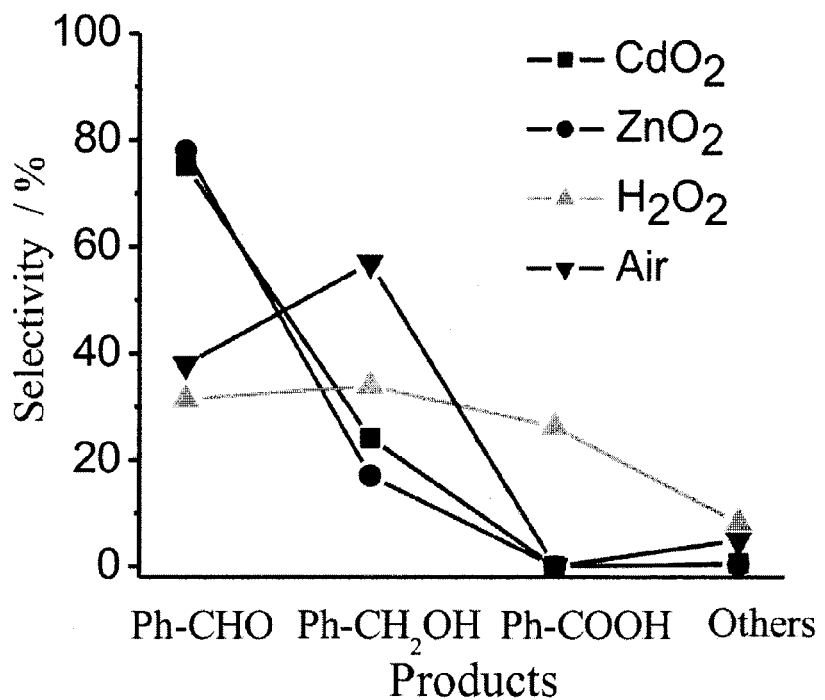

FIG. 9 depicts the selectivity towards different oxidation products, while $CdO_2$, $ZnO_2$, $H_2O_2$ and air are used as oxidants under comparable experimental conditions.

Figure 10:
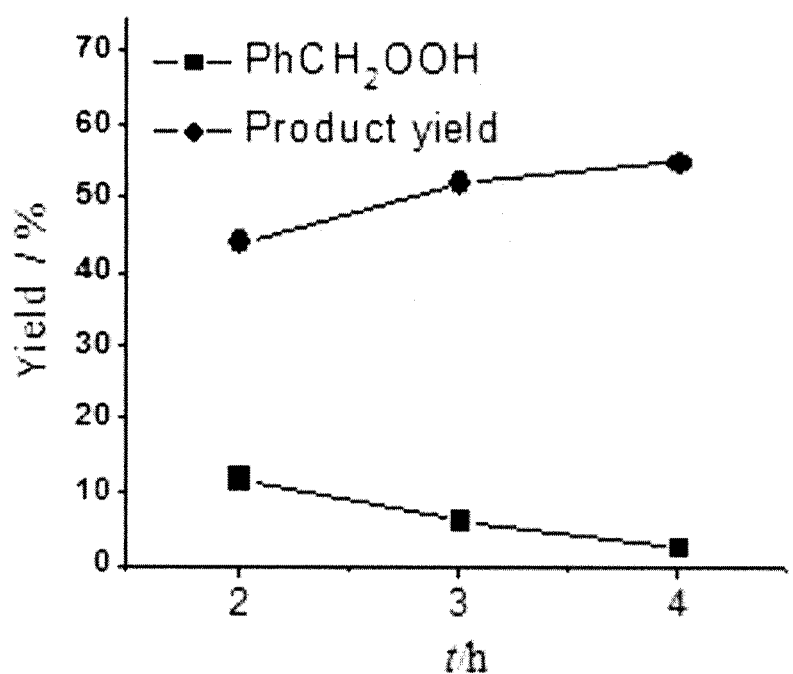

FIG. 10 depicts total yield and the amount of benzyl hydroperoxide present in the reaction mixture of toluene and $ZnO_2$ at 180° C. at various time intervals.

DETAILED DESCRIPTION OF THE DISCLOSURE

The present disclosure relates to a method of oxidizing an aliphatic C—H bond in an organic compound, said method comprising acts of mixing the organic compound with metal peroxide nanoparticle selected from group comprising cadmium peroxide or zinc peroxide to obtain reaction mixture; and heating the reaction mixture to obtain oxidized product.

The present disclosure also relates to use of metal peroxide nanoparticle selected from group comprising $CdO_2$ or $ZnO_2$, for oxidizing an aliphatic C—H bond in an organic compound to obtain oxidized product.

In an embodiment of the disclosure, the organic compound has atleast one methyl group and is selected from group comprising aromatic compound and aliphatic compound.

In another embodiment of the disclosure, the organic compound is selected from group comprising toluene, cyclohexane and n-hexane, preferably toluene.

In yet another embodiment of the disclosure, the metal peroxide nanoparticle is optionally doped with nickel.

In still another embodiment of the disclosure, the organic compound is at volume ranging from about 5 ml to about 18 ml, preferably about 15 ml; the metal peroxide nanoparticle is at amount ranging from about 200 mg to about 500 mg, preferably about 300 mg for zinc peroxide and about 440 mg for cadmium peroxide; and the metal peroxide nanoparticle has diameter ranging from about 5 nm to about 10 nm.

In still another embodiment of the disclosure, the heating is carried out at temperature ranging from about 140° C. to about 200° C., preferably about 160° C. to about 180° C., for time duration ranging from about 1 h to about 15 h, preferably about 4 h to about 12 h.

In still another embodiment of the disclosure, the oxidized product is selected from group comprising benzaldehyde, benzyl alcohol, methyldiphenylmethane and diphenyl ethane or combinations thereof, preferably benzaldehyde.

In still another embodiment of the disclosure, selectivity of the benzaldehyde is ranging from about 60% to about 95% of total percent yield ranging from about 70% to about 32% with respect to the total peroxide used.

In still another embodiment of the disclosure, the oxidized product is separated by technique selected from group comprising centrifugation and chromatography or combination thereof.

In still another embodiment of the disclosure, the oxidized product is estimated by Nuclear magnetic resonance (NMR) or Gas chromatography-mass spectrometry (GC-MS).

In another embodiment of the disclosure, the formula $MO_2$ represents metal peroxide, wherein M is the metal cadmium or zinc. Further, CdO represents cadmium oxide, ZnO represents zinc oxide, $CdO_2$ represents cadmium peroxide, $ZnO_2$ represents zinc peroxide, $H_2O_2$ represents hydrogen peroxide, Ph-CHO represents benzaldehyde, Ph-$CH_2$OH represents benzyl alcohol, Ph-COOH represents benzoic acid, Ph-$CH_2$OOH represents benzyl hydroperoxide, Ni represents nickel and $ZnO_{0.8}Ni_{0.2}O_2$ represents nickel doped zinc peroxide.

The present disclosure relates to activation of C—H bond in organic compounds such as toluene by use of the metal peroxides $CdO_2$ and $ZnO_2$ as the oxygen source. It has several advantages over other methods. Unlike many of the oxidation protocols involving biphasic reactions or solvents, the instant reaction is solvent-free. The reaction time is about 4 h which is considerably shorter than that of other methods which require about 1-3 days. In the absence of any catalyst, catalyst poisoning and regeneration is avoided. Besides, $CdO_2$ and $ZnO_2$ are readily produced and are not dangerous unlike organic peroxides. The monoxides produced in the instant reaction are reconverted to their respective peroxides by treatment with $H_2O_2$.

Further, the oxidation products of the organic compound toluene are predominantly benzaldehyde and lower amounts of benzyl alcohol. Other oxidation products, if present, are at an amount lesser than about 5%.

In an embodiment of the disclosure, oxidation yields are calculated with respect to peroxide by stoichiometry. Selectivity of the reaction products are calculated based on GCMS/NMR data.

In an embodiment of the disclosure, nanoparticles of the metal peroxides $CdO_2$ and $ZnO_2$ decompose at a relatively lower temperature (<200° C.) giving out oxygen and the respective metal oxide. They have the lowest decomposition temperatures amongst the stable metal peroxides. Hence, these materials are sources of oxygen for the oxidation of toluene.

Figure 1:
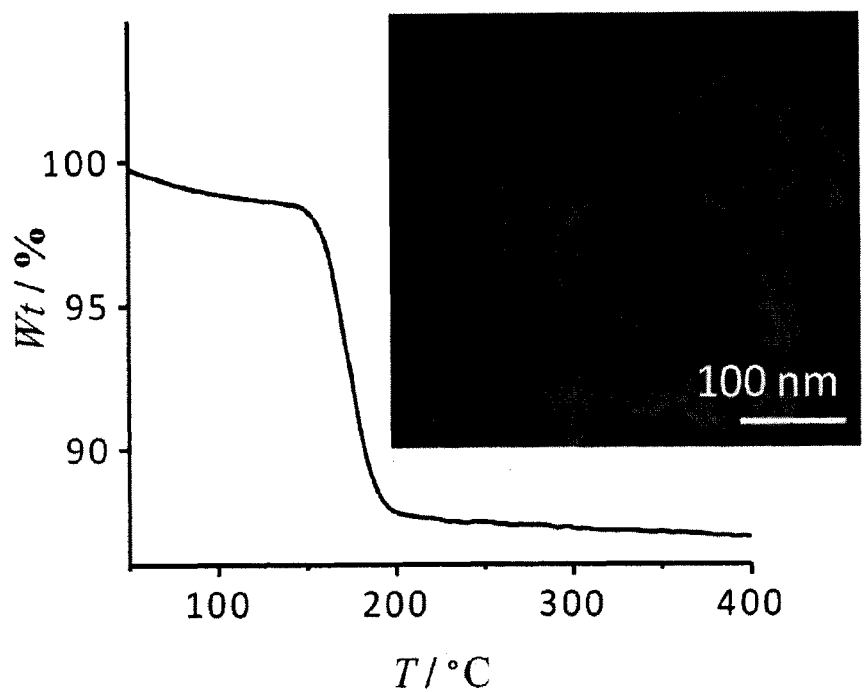
FIG. 1A depicts Thermo Gravimetric Analysis data showing the decomposition profiles of nanoparticles of $CdO_2$. Insets show the SEM images of the particles.
FIG. 1B depicts Thermo Gravimetric Analysis data showing the decomposition profiles of nanoparticles of $ZnO_2$. Insets show the SEM images of the particles.
Figure 1:
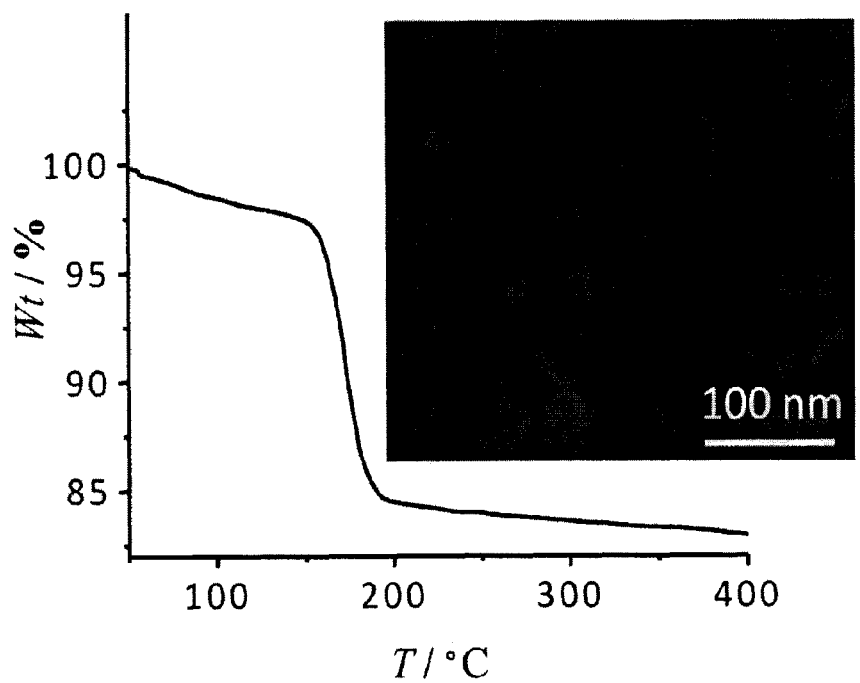

In another embodiment of the disclosure, nanoparticles of $ZnO_2$ and $CdO_2$ are prepared by the reaction of ZnO and CdO with excess $H_2O_2$ at about 80° C. (1 h) and about 100° C. (12 h) respectively. The peroxide particles so obtained are crystalline with diameters approximately in the 5-10 nm range. The BET surface areas of the $ZnO_2$ and $CdO_2$ particles are about 54 m²/g and about 46 m²/g respectively. The smaller size of the nanocrystals may influence its decomposition and hence the release of oxygen. The decomposition temperatures of the peroxides are in the range of about 160-180° C. as revealed by thermogravimetric analysis (FIG. 1). In an experiment to oxidize toluene, a predetermined amount of toluene and metal peroxide are sealed in a teflon-lined autoclave and heated at the desired temperature for a fixed period of time in a preheated air oven. The product obtained is characterized by GC-MS and NMR spectroscopy.

In another embodiment of the disclosure, nanoparticles of $ZnO_2$ and $CdO_2$ are doped with Nickel. In Ni doped $ZnO_2$, some of the Zn is replaced by nickel.

Figure 2:
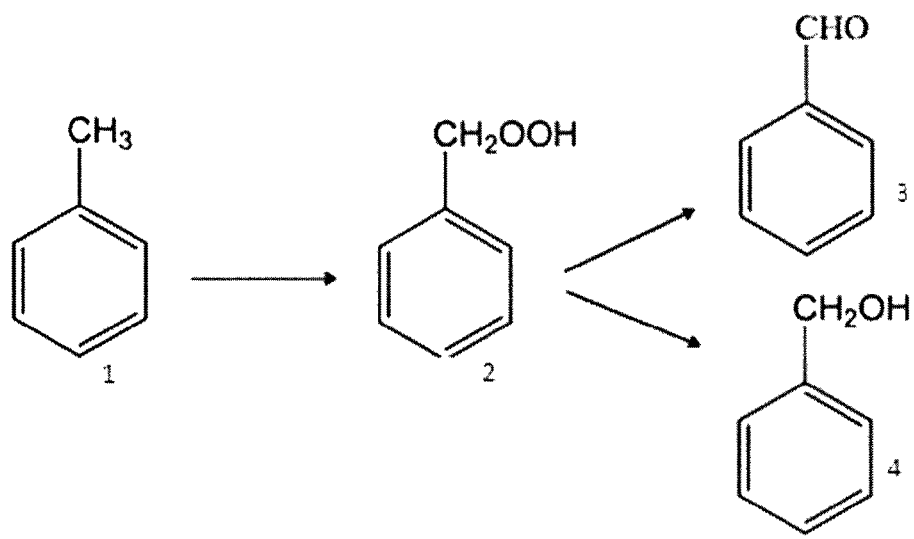
FIG. 2 depicts selective oxidation of toluene, wherein 1 represents toluene, 2 represents benzyl hydroperoxide, 3 represents benzaldehyde and 4 represents benzyl alcohol.

In an embodiment of the disclosure, the oxidation of toluene by $MO_2$ is by selective oxidation. In the instant disclosure, selective oxidation implies oxidation of the aliphatic CH group in an organic compound, while the aromatic CH groups remain intact. FIG. 2 explains selective oxidation, wherein the $CH_3$ group of toluene is converted to benzyl hydroperoxide, which further converts to benzaldehyde and benzyl alcohol. This is called selective oxidation, as the oxidation with $MO_2$ such as $ZnO_2$ and $CdO_2$ can oxidize the entire compound to form $CO_2$ and $H_2O$ or it can oxidise the benzyl group as well; instead it selectively oxidizes only the $CH_3$ group.

In an embodiment of the disclosure, the peroxide decomposition on completion leaves behind CdO or ZnO. However, cadmium or zinc can be collected back after the reaction as CdO and ZnO and can be recycled. Hence, the exposure of cadmium or zinc is reduced.

The following examples further elaborate and illustrate the aspects of the present disclosure. However, these examples should not be construed to limit the scope of the instant disclosure.

EXAMPLES

Example 1

Synthesis of $ZnO_2$ and $CdO_2$ Nanoparticles

Figure 3:
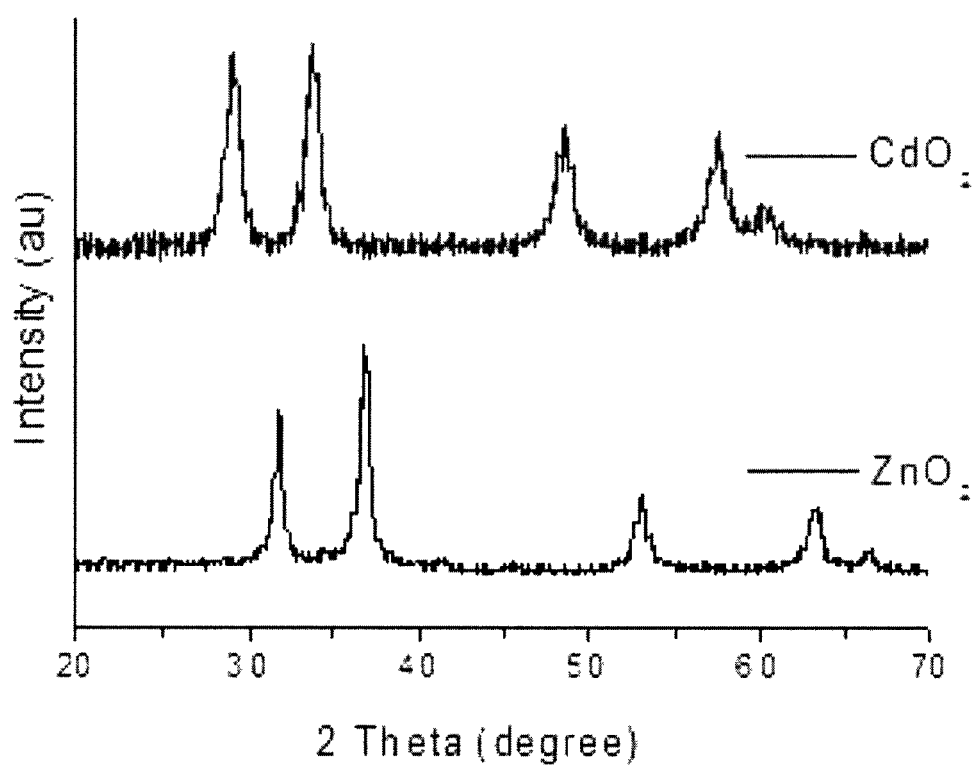
FIG. 3 depicts XRD pattern of powder containing $CdO_2$ (JSPDS: 78-1125, a=5.386 Å) and $ZnO_2$ (JCPDS: 78-1124, a=4.902 Å) nanoparticles confirming purity.

The $MO_2$ (M=Cd, Zn) nanoparticles are synthesized by the treatment of corresponding monoxides with $H_2O_2$. Typically, about 2 g of ZnO is dispersed in about 20 ml of $H_2O$ under constant stirring at about 80° C. About 10 ml of about 30% $H_2O_2$ is added to this dispersion and reacted for about 1 h to finally obtain $ZnO_2$. Conversion of CdO (about 2 g dispersed in about 20 ml of $H_2O$) to $CdO_2$ is slower and takes place when about 10 ml of about 30% $H_2O_2$ is added drop-wise to the CdO dispersion over a period of about 12 h under the same conditions viz. under constant stirring at about 80° C. At the end of the reaction, the as synthesized nanoparticles are separated from the solution by centrifugation at about 4000 rpm for about 5 min. As collected products are washed with water twice, followed by an ethanol-wash and air-dried at about 60° C. XRD pattern of the powder so obtained is illustrated in FIG. 3 which confirms purity of $CdO_2$ (JSPDS: 78-1125, a=5.386 Å) and $ZnO_2$ (JCPDS: 78-1124, a=4.902 Å) nanoparticles.

Example 2

Synthesis of Ni-doped $ZnO_2$

Figure 4:
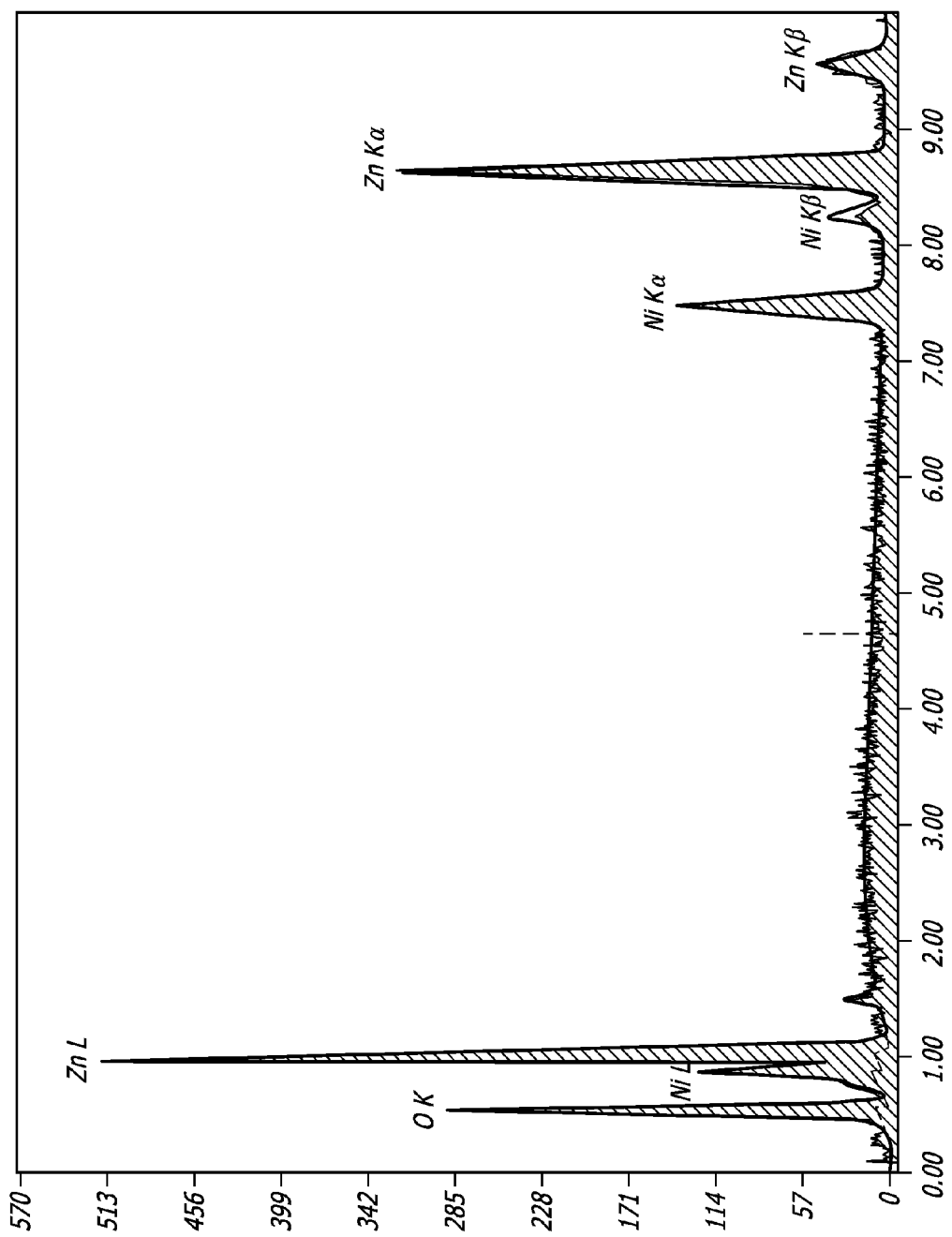
FIG. 4 depicts EDS spectrum of the Ni doped $ZnO_2$ sample. Detailed elemental analysis of the sample at various positions shows near uniform distribution of Ni.

Zinc acetate (about 8 mmol) and nickel acetate (about 2 mmol) are dissolved in water (about 40 ml) and about 30% $H_2O_2$ (about 10 ml) is added. KOH solution is then added dropwise, instantly yielding a light greenish-white precipitate of Ni-doped $ZnO_2$. The Ni content is estimated in the sample to be about 17-19% from energy-dispersive X-ray spectroscopic (EDS) analysis (FIG. 4). Analysis of the sample at various positions showed near uniform distribution of Ni.

Example 3

Oxidation Reactions

Oxidation reactions of toluene by metal peroxides ($ZnO_2$ and $CdO_2$) are carried out in teflon lined autoclaves. About 15 ml of toluene (about 139 mmol) and about 3 mmol of metal peroxide (about 300 mg of $ZnO_2$ or about 440 mg of $CdO_2$) are sealed in about 20 ml autoclave and kept inside an oven which is preheated and maintained to the desired temperature (about 140-180° C.) for definite time interval (about 1-12 h). The reaction mixture within the autoclave is thereby maintained at a temperature ranging from about 140-180° C. At the end of the reaction, the autoclave is cooled to room temperature (about 25° C.-30° C.) naturally. The amount of the reaction products in the reaction mixture is estimated and the reaction products are separated from the oxides by centrifugation or chromatography such as column chromatography using a $SiO_2$ column to yield pure products.

Characterization:

Identity and purity of the peroxides and their decomposition products (after the toluene oxidation reaction) are established with powder X-ray diffraction (XRD) using Bruker D8 diffractometer equipped with a copper radiation source (λ=1.5406 Å). Thermo gravimetric analysis (TGA) of the peroxides is conducted with Perkin Elmer thermogravimetry analyzer. The identification and quantitative estimation of the toluene oxidation product are carried out with NMR (Bruker AV-400) and GC-MS (Shimadzu GC-2010) techniques.

Notably analysis of the reaction product is carried out immediately after the reaction in order to avoid further atmospheric oxidation of products. (Note: Cleaning of teflon vessel with Nitric acid should be avoided for cleaner products). Similar reactions are carried out in presence of $H_2O_2$ for purpose of comparison.

In the reactions, the amount of peroxide used is substoichiometric with respect to the amount of toluene (about 15 ml). Therefore the yields reported here are calculated based on the amount of metal peroxide that gets converted to the products reported (refer to table 2 below).

Blank reaction:

In all the oxidation reactions of toluene that are carried out, there is a possibility of aerial oxidation since the reaction vessel is partly filled with air, in addition to the dissolved oxygen. Therefore to estimate the blank baseline yield, the oxidation products that arise due to the presence of oxygen in the reaction vessel are carefully analyzed. This is further evaluated since recent studies have shown that such oxidation can take place at low temperatures as well [for ex.: at about 160° C.]. However, on evaluation it is observed that the product so obtained is extremely small (about ~5%) in comparison to the peroxide reaction, and yielded comparable amounts of benzaldehyde, benzyl alcohol and other oxidation products such as methyldiphenylmethane and isomers of diphenyl ethane. Therefore the effect of dissolved and aerial oxygen enclosed in the reaction vessel is neglected.

Example 3a

The reaction of toluene with $CdO_2$ nanoparticles (as indicated in Example 3) is carried over different periods at various temperatures up to about 180° C., for ex.: about 140° C., about 160° C., about 180° C. etc., till the peroxide decomposition is complete, leaving CdO behind. At about 180° C., the reaction is complete within about 4 h, wherein the entire peroxide is converted to the oxide. The GC-MS data of the reaction products obtained at about 180° C. and about 4 h is illustrated in FIG. 5. Under these reaction conditions, toluene is oxidized to yield predominantly benzaldehyde (about 69%), along with some benzyl alcohol (about 26%) and a minute quantity (about 5%) of methyldiphenylmethane and isomers of diphenyl ethane (Tables 1 and 2). Benzoic acid and other oxidation products are not formed in the reaction. The reaction of the peroxide with toluene yields benzaldehyde and a water molecule. The yield of the oxidation products is estimated to be about 70%, with a selectivity of about 69% for benzaldehyde.

An examination of the reaction profile of the $CdO_2$ during the first 4 h at about 180° C. shows that the reaction proceeds gradually yielding increasing amounts of the reaction products (FIG. 6a). However, selectivity towards benzaldehyde is higher during the initial period of reaction. The gradual conversion of toluene is found at other reaction temperatures as well. It takes about 12 h for completion of the reaction at about 160° C. and the reaction is much slower at about 140° C. FIG. 6b shows the selectivity and yield of the oxidation reactions at various temperatures after about 4 h of reaction. It is observed that selectivity towards benzaldehyde is higher at lower temperatures as well as in the initial stages of the reaction.

TABLE 1

Comparison of oxidation products of toluene by $CdO_2$ and $ZnO_2$ nanoparticles obtained under different experimental conditions.[a]

| Condition | | Yield[b] | Selectivity [%] | | |
|---|---|---|---|---|---|
| T/° C. | t/h | (%) | Benzaldehyde | Benzyl alcohol | Other[c] |
| $CdO_2$ about 180 | about 4 | about 70 | about 69 | about 26 | about 5 |

TABLE 1-continued

Comparison of oxidation products of toluene by $CdO_2$ and $ZnO_2$ nanoparticles obtained under different experimental conditions.[a]

| Condition | | Yield[b] | Selectivity [%] | | |
|---|---|---|---|---|---|
| T/° C. | t/h | (%) | Benzaldehyde | Benzyl alcohol | Other[c] |
| about 160 | about 12 | about 57 | about 71 | about 28 | about 1 |
| $ZnO_2$ about 180 | about 4 | about 58 | about 80 | about 16 | about 4 |
| about 160 | about 12 | about 68 | about 76 | about 21 | about 3 |

[a]Oxidation of residual air in the reaction vessel is found to yield negligible quantities of benzaldehyde and other products.
[b]The stoichiometric oxidation yields are calculated with respect to peroxide.
[c]'Other' includes mixtures of methyldiphenylmethane or isomers of diphenyl ethane.

TABLE 2

Oxidation products of toluene by $CdO_2$ and $ZnO_2$ nanoparticles under various experimental conditions[a].

| Sl. No. | Condition | | Yield[b] | Selectivity (%) | | | |
|---|---|---|---|---|---|---|---|
| | Temperature (° C.) | Time (h) | (%) | Benzaldehyde | Benzyl alcohol | Benzoic acid | Others[c] |
| $CdO_2$ | | | | | | | |
| 1 | about 180 | about 4 | about 70 | about 69 | about 26 | about 0 | about 5 |
| | | about 3[a] | about 51 | about 73 | about 25 | about 0 | about 1 |
| | | about 2[a] | about 43 | about 72 | about 24 | about 0 | about 4 |
| | | about 1[a] | about 30 | about 82 | about 17 | about 0 | about 1 |
| | about 160 | about 4[a] | about 36 | about 75 | about 25 | about 0 | about 0 |
| | | about 12 | about 57 | about 71 | about 28 | about 0 | about 1 |
| $ZnO_2$ | | | | | | | |
| 2 | about 180 | about 4 | about 58 | about 80 | about 16 | about 0 | about 4 |
| | | about 3[a] | about 49 | about 80 | about 16 | about 0 | about 4 |
| | | about 2[a] | about 41 | about 84 | about 12 | about 0 | about 4 |
| | | about 1[a] | about 33 | about 88 | about 11 | about 0 | about 1 |
| | about 160 | about 4[a] | about 32 | about 92 | about 8 | about 0 | about 0 |
| | | about 12 | about 68 | about 76 | about 21 | about 0 | about 3 |

[a]The decomposition of peroxides in the reaction medium is slower than in air and these data correspond to incomplete decomposition of metal peroxides.
NOTE:
Yields presented here are calculated based on the initial amount of peroxide taken for the reaction.
[b]The stoichiometric oxidation yields are calculated with respect to peroxide.
[c]'Other' includes mixtures of methyldiphenylmethane or isomers of diphenyl ethane.

Example 3b

The oxidation of toluene with $ZnO_2$ nanoparticles is carried as per Example 3. When the reaction is carried out at about 180° C. for about 4 h, about 58% of the peroxide is converted to the oxidation products (Table 1), consisting mainly of benzaldehyde (about 80%) and benzyl alcohol (about 16%) and minute quantity (about 4%) of methyldiphenylmethane and isomers of diphenyl ethane. $ZnO_2$ is converted to ZnO and no benzoic acid is detected among the oxidation products. The yield is increased at lower reaction temperature, albeit at a slower rate. For example, the decomposition of $ZnO_2$ is not complete in about 4 h at a temperature of about 160° C., and the yield is only about 32%. The yield increases to about 68%, when the reaction is carried out for about 12 h, concurrent with the complete decomposition of the peroxide. The oxidation product contained about 76% benzaldehyde, about 21% benzyl alcohol and trace amounts of other products including methyldiphenylmethane or isomers of diphenyl ethane.

The results obtained with $ZnO_2$ and $CdO_2$ nanoparticles are provided in FIGS. 7a and 7b. $CdO_2$ nanoparticles function well in terms of product yields even after about 4 h. Further, $ZnO_2$ is also good at lower temperatures.

Decomposition of the $ZnO_2$ during the oxidation reaction is depicted in FIG. 8, wherein: XRD patterns of the solid product obtained after toluene oxidation carried out at about 180° C., in presence of $CdO_2$ after about 1 h and about 2 h. Unlike fast aerial decomposition of the peroxides, their decomposition in the reaction medium at same temperature is much slower.

As illustrated in tables 1 and 2 the reaction products obtained on oxidation of toluene with $ZnO_2$ and $CdO_2$ are different. For example, at 180° C., 70% yield is obtained with $CdO_2$, while 58% yield is obtained with $ZnO_2$. In addition, the distribution of the products is also different in both the cases. Similar differences are observed at different temperatures. These differences are due to catalytic effect of ZnO and CdO. Thus, in addition to supplying oxygen for the oxidation reactions, the zinc peroxides' and cadmium peroxides' reactions are also catalytic.

Example 4

The oxidation of toluene with Nickel-doped $ZnO_2$ nanoparticles is carried out as per Example 3. The reaction is carried out at about 140° C. for about 12 h resulting in a yield of about 49% (Table 3), consisting of about 80% of benzaldehyde and about 20% benzyl alcohol.

TABLE 3

Results of oxidation reaction conducted at a temperature of 140° C. using Ni incorporated $ZnO_2$

| Condition | | Yield[a] | Selectivity [%] | | |
|---|---|---|---|---|---|
| T/° C. | t/h | (%) | Benzaldehyde | Benzyl alcohol | Other[c] |
| $Zn_{0.8}Ni_{0.2}O_2$ at about 140 | about 12 | about 49 | about 80% | about 20% | about 0 |
| $ZnO_2$ at about 140 | about 12 | about 4-5% | about 85% | about 15% | about 0 |

[a]The stoichiometric oxidation yields are calculated with respect to peroxide.

From the table 3 it is seen that the oxidation reaction of toluene using $ZnO_2$ is unproductive at about 140° C. Doping zinc peroxide with nickel reduces the decomposition temperature of the metal peroxide. Therefore, reaction for oxidising toluene is made productive at about 140° C. by doping zinc peroxide with nickel.

Example 5

In order to verify the role of the peroxide and to understand the difference in the oxidation process of cadmium peroxide and zinc peroxide with that of oxidation reaction by $H_2O_2$, experiments using hydrogen peroxide as well as air as oxidizing agents are carried out (FIG. 9 and Table 4). The oxidation reaction is carried out in presence of equivalent amount of $H_2O_2$ (as that of $CdO_2$ or $ZnO_2$) under identical conditions as Example 3. Similarly, aerial oxidation is carried out by taking advantage of the fact that in a larger autoclave, a small amount of toluene filling leaves large volume of air (and therefore oxygen) usable for oxidation. The aliquots of a reaction mixture is separated from the solid oxygen precursor by centrifugation at about 3000 rpm for about 3 minutes and subjected to analysis.

In these cases, selectivity towards the products is vastly different from that with metal peroxides. $H_2O_2$ yielded nearly equal proportions of benzaldehyde, benzyl alcohol and benzoic acid, while the aerial oxidation primarily yielded benzyl alcohol. Comparison of the $MO_2$ oxidation reaction with that of $H_2O_2$ and aerial oxidation is presented in FIG. 9 and Table 4, wherein the selectivity towards different oxidation products, while $CdO_2$, $ZnO_2$, $H_2O_2$ and air are used as oxidants under comparable experimental conditions.

TABLE 4

Comparison of oxidation products of toluene by oxidation with $CdO_2$, $ZnO_2$, $H_2O_2$ and air obtained under comparable experimental conditions employed in Example 3.

| Sl. No | Reagent | Condition Temperature (° C.) | Time (h) | Selectivity (%) | | | |
|---|---|---|---|---|---|---|---|
| | | | | Benzaldehyde | Benzyl alcohol | Benzoic acid | Others |
| 1 | $CdO_2$ | about 180 | about 4 | about 69 | about 26 | about 0 | about 5 |
| 2 | $ZnO_2$ | about 180 | about 4 | about 80 | about 16 | about 0 | about 4 |
| 3 | $H_2O_2$ | about 180 | about 4 | about 31.4 | about 33.9 | about 26.3 | about 8.2 |
| 4 | Air | about 180 | about 4 | about 38 | about 57 | about 0 | about 5 |

The difference in the product yields and the selectivity found with $CdO_2$ and $ZnO_2$ nanoparticles indicates a more specific role for the peroxide in the reaction. The decomposition of the peroxides is slower in the reaction medium compared to that in air. This could be due to the formation of a hydroperoxide intermediate, since benzaldehyde and $H_2O$ are obtained in equal proportions. The hydroperoxide is isolated, and its proportion is observed to vary with yield of the aldehyde (FIG. 10). Estimation of benzylhydroperoxide intermediate is depicted in FIG. 10, wherein total yield and the amount of benzyl hydroperoxide present in the reaction mixture of toluene and $ZnO_2$ at about 180° C. at various time intervals is showcased. The amount of benzyl hydroperoxide initially increases and then decreases as more of it is converted to products.

We claim:

1. A method of oxidizing an aliphatic C—H bond in an organic compound, said method comprising acts of mixing the organic compound with metal peroxide nanoparticle selected from group comprising cadmium peroxide or zinc peroxide to obtain reaction mixture; and heating the reaction mixture to obtain oxidized product.

2. A method of using metal peroxide nanoparticle selected from group comprising $CdO_2$ or $ZnO_2$, for oxidizing an aliphatic C—H bond in an organic compound, said method comprising act, of mixing the nanoparticle with the organic compound to oxidize said aliphatic C—H bond.

3. The method as claimed in claims 1 or 2, wherein the organic compound has at least one methyl group and is selected from group comprising aromatic compound and aliphatic compound.

4. The method as claimed in claims 1 or 2, wherein the organic compound is selected from group comprising toluene, cyclohexane and n-hexane.

5. The method as claimed in claims 1 or 2, wherein the metal peroxide nanoparticle is optionally doped with nickel.

6. The method as claimed in claims 1 or 2, wherein the organic compound is at volume ranging from about 5 ml to about 18 ml; the metal peroxide nanoparticle is at amount ranging from about 200 mg to about 500 mg; and the metal peroxide nanoparticle has diameter ranging from about 5 nm to about 10 nm.

7. The method as claimed in claims 1 or 2, wherein the heating is carried out at temperature ranging from about 140° C. to about 200° C., for time duration ranging from about 1 hour to about 15 hours.

8. The method as claimed in claims 1 or 2, wherein the oxidized product is selected from group comprising benzaldehyde, benzyl alcohol, methyldiphenylmethane and diphenyl ethane or combinations thereof.

9. The method as claimed in claims 1 or 2, wherein selectivity of the benzaldehyde is ranging from about 60% to about 95% of total percent yield ranging from about 70% to about 32% with respect to the total peroxide used.

10. The method as claimed in claim 1, wherein the oxidized product is separated by technique selected from group comprising centrifugation and chromatography or combination thereof.

11. The method as claimed in claim 1, wherein the oxidized product is estimated by Nuclear magnetic resonance (NMR) or Gas chromatography-mass spectrometry (GC-MS).

12. The method as claimed in claim 1 or 2, wherein the organic compound is toluene.

13. The method as claimed in claim 1 or 2, wherein the organic compound is at a volume of about 15 ml; the zinc peroxide nanoparticle is at an amount of about 300 mg and the cadmium peroxide nanoparticle is at an amount of about 440 mg.

14. The method as claimed in claim 1 or 2, wherein the heating is carried out at temperature ranging from about 160° C. to about 180° C., for time duration ranging from about 4 hours to about 12 hours.

15. The method as claimed in claim 1 or 2, wherein the oxidized product is benzaldehyde.

* * * * *